United States Patent [19]

Citrin

[11] 4,342,407
[45] Aug. 3, 1982

[54] LIQUID DISPENSING APPARATUS

[75] Inventor: Paul S. Citrin, Danbury, Conn.

[73] Assignee: Dynatech Laboratories, Incorporated, Alexandria, Va.

[21] Appl. No.: 173,628

[22] Filed: Jul. 30, 1980

Related U.S. Application Data

[63] Continuation of Ser. No. 821,836, Aug. 4, 1977, abandoned, which is a continuation-in-part of Ser. No. 595,005, Jul. 11, 1975, Pat. No. 4,058,146.

[51] Int. Cl.³ .......................... B65B 3/06; F16C 55/14
[52] U.S. Cl. .................................... 222/485; 222/504; 91/417 R; 251/5; 251/7
[58] Field of Search .................... 222/330, 485, 504; 141/238, 242, 243, 244; 251/7, 4, 6, 8, 9, 10; 422/100; 91/417 R

[56] References Cited

U.S. PATENT DOCUMENTS

| | | | |
|---|---|---|---|
| 11,300 | 1/1893 | Donally | 251/7 X |
| 686,087 | 11/1901 | Klein et al. | 91/417 R |
| 1,652,537 | 12/1927 | Lewis | 251/4 |
| 2,291,267 | 7/1942 | Weiner | 251/9 X |
| 2,985,341 | 5/1961 | Howell | 251/4 X |
| 3,248,011 | 4/1966 | Brodsky et al. | 251/7 X |
| 3,264,067 | 8/1966 | Alderfer | 251/7 X |
| 3,982,724 | 9/1976 | Citrin | 251/7 |
| 4,030,640 | 6/1977 | Citrin et al. | 222/504 X |

FOREIGN PATENT DOCUMENTS 1350576  4/1974  United Kingdom ............. 91/417 R Primary Examiner—Robert J. Spar
Assistant Examiner—Frederick R. Handren
Attorney, Agent, or Firm—LeBlanc, Nolan, Shur & Nies

[57] ABSTRACT

Apparatus for control of multiple liquid dispensing providing accurate metering, close spacing of the fluids dispensed and rapid cycling. One embodiment contemplates transferring liquids from a multiplicity of containers to a corresponding multiplicity of wells in a microtitration test tray, and includes a multiplicity of resilient conduits extending from the containers into a common pinch type valve that clamps the ends of the conduits closed or permits them to open for liquid discharge.

8 Claims, 6 Drawing Figures

LIQUID DISPENSING APPARATUS

This is a continuation of Ser. No. 821,836 filed Aug. 4, 1977, now abandoned, which in turn is a continuation-in-part of application Ser. No. 595,005 filed July 11, 1975 for *Method and Apparatus for Transferring Liquid*, now U.S. Pat. No. 4,058,146 issued Nov. 11, 1977.

The invention relates to liquid dispensing apparatus and particularly to such having special valve arrangements for controlling dispensing of liquid from a number of individual elastomeric conduits.

The invention in its preferred embodiment will be described as incorporated in apparatus adapted for solving problems in antibiotic susceptibility testing wherein it is required that accurately metered similar amounts of a multiplicity of different liquids be transferred at the same time to identified individual wells or cells of a microtitration test tray or the like, but it is not limited to this usage.

In carrying out a preferred utilization of the invention liquids to be tested are provided in quantity in individual supply containers such as test tubes carried on a special rack which is indexed in a system so that each test tube occupies a location on the rack corresponding to the location of wells of a receiver microtitration test tray or the like that is mounted in a remote position in the system. Preferably the system is supported within a housing having a loading door through which the rack is so inserted that the containers are connected into an elastomeric conduit arrangement leading to a special dispensing valve structure at which the test tray or the like is located.

The major object of the invention is to provide a novel valve assembly for controlling the dispensing of liquids transmitted through one or more individual resilient conduits of elastomeric material.

A further object of the invention is to provide a novel liquid dispensing apparatus wherein liquid is transmitted through a plurality of separate conduits each having resilient discharge end regions providing substantially identical resistance to liquid flow at least, and containing a special pinch valve arrangement whereby selective discharge from said end regions is efficiently effectively controlled by pinch valve means at the extreme tips.

Another object of the invention is to provide a liquid dispensing apparatus wherein liquid is transmitted through a plurality of separate resilient conduits and the discharge ends of the conduits are disposed within a novel valve arrangement between relatively movable members operable to block or permit opening of said discharge ends for selective dispensing.

Further objects will appear in connection with the appended claims and the annexed drawings.

In its preferred embodiment the invention will be described as incorporated in apparatus for the control of the simultaneous dispensing of multiple fluids to the closely spaced wells of a test tray which may be a microtitration plate of the type disclosed in U.S. Pat. No. 3,356,462 issued Dec. 5, 1967 to N. M. Cooke et al.

Figures 1, 1A:
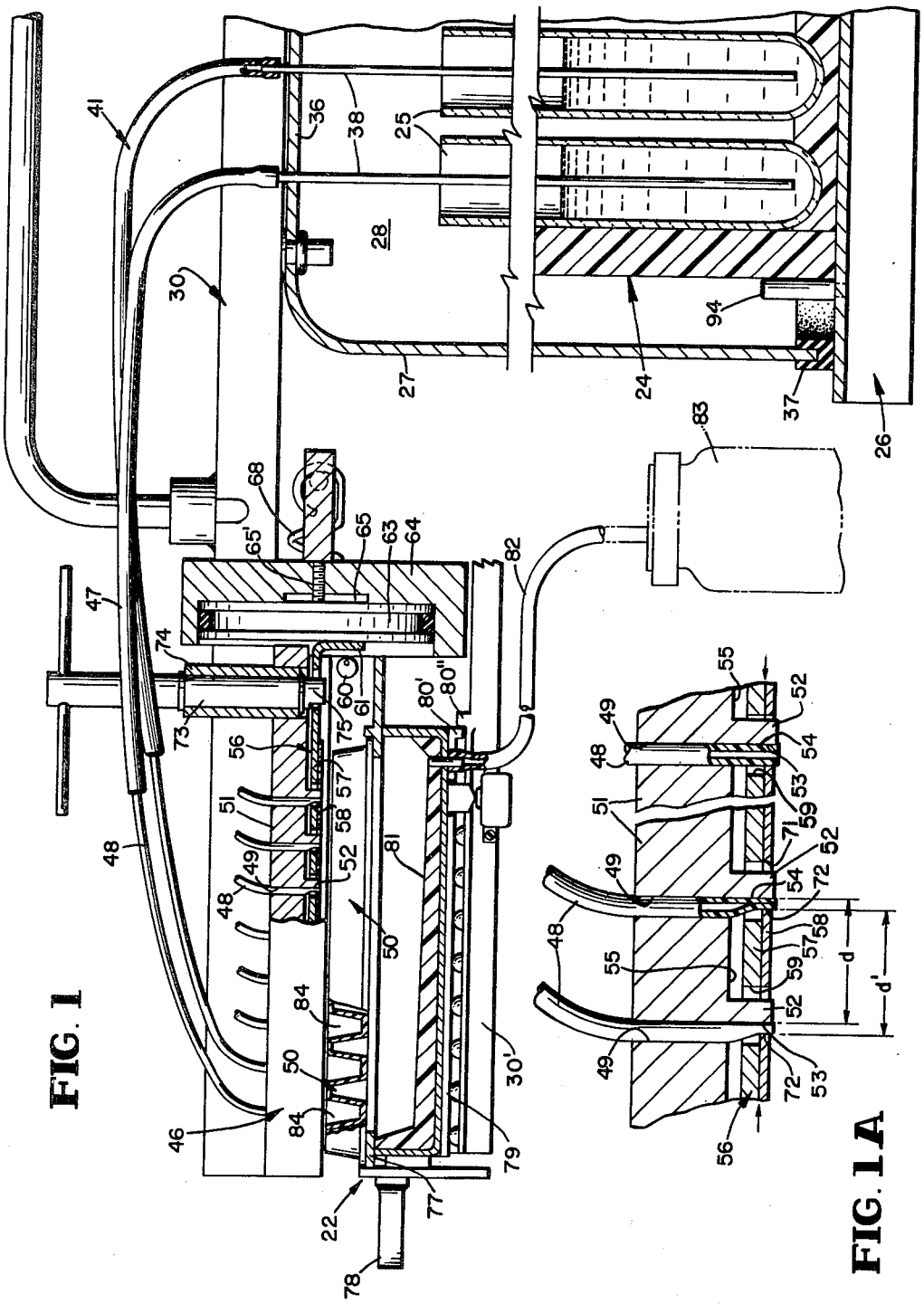
FIG. 1 is a fragmentary view mainly in section showing the pinch valve assembly according to a preferred embodiment.
FIG. 1A is an enlarged fragmentary view in section broken for showing valve detail and mode of operation.

As shown in FIG. 1 the liquids to be dispensed may be contained in a multiplicity of containers 25 mounted on a rack 24 carried by a platform 26. The platform is sealingly connected to a shell 27 enclosing the containers and providing a fluid pressure chamber 28.

Shell 27 is fixedly mounted on a housing frame 30. Preferably shell 27 is an integral sheet metal unit having a top wall 36 and a resilient seal gasket 37 around the rim at its lower open end. A multiplicity of stiff parallel stainless steel tubes 38 of the same length extend vertically downwardly within the shell to terminate in open ends within containers 25. Each tube 38 extends pressure tight through an opening in wall 36 for receiving the end of flexible tubing indicated at 41.

In practice adjacent stiff tubes 38 are equally spaced and the number, arrangement and spacing correspond exactly to the number, arrangement and spacing of the containers 25 on the rack 24. Thus if there are ninety-six containers on the rack in eight rows of twelve each, the tubes 38 are arranged in the same distribution.

Figure 2:
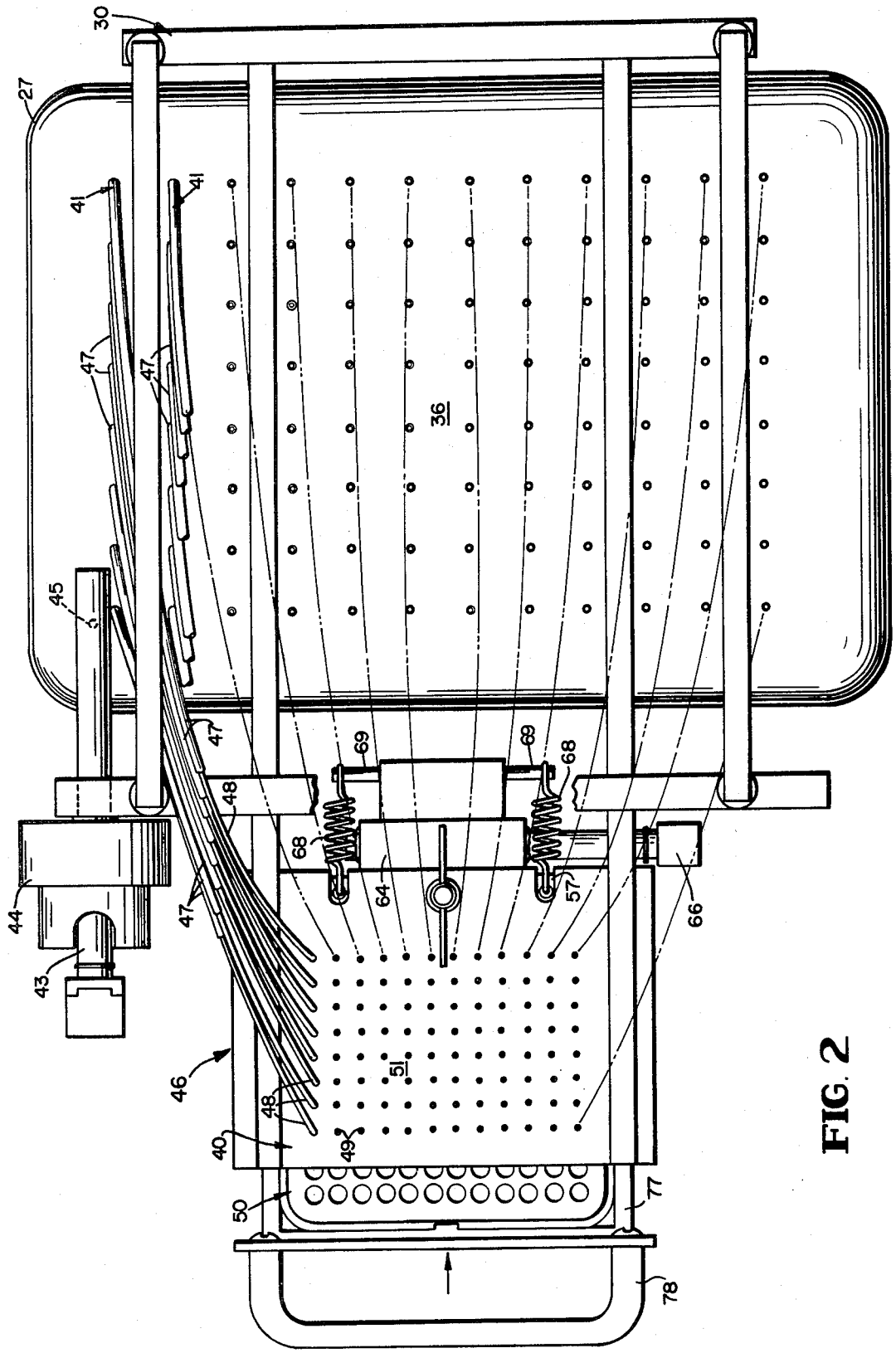
FIG. 2 is a top plan view showing a conduit system leading to the pinch valve assembly.

As shown in FIG. 2, fluid pressure in the form of pressurized pure air may be introduced into chamber 28 through a pipe connection 43 having a filter 44, the inlet to chamber 28 being indicated at 45.

As shown in FIGS. 1 and 2, the conduit system comprising ninety-six individual lengths of flexible tubing 41 each connected to a tube 38 extends from the top of shell 27 to a dispensing valve assembly at 46. In this embodiment each length of flexible tubing 41 consists in succession of a large diameter initial section 47 and a small diameter resilient wall discharge section 48 at the valve end. The small sections are each very accurately of the same length and the same uniform internal diameter. This ensures that each tubing 41 regardless of its overall length or the diameter of the large diameter section offers identical resistance to liquid flow therethrough. The large diameter sections may be of the same internal diameter but they are of random length. In practice in a successfully operable system, the internal diameter of each small section is in the order of 0.032 inches while the internal diameter of the large diameter section is a minimum of twice that of the small diameter section. In some embodiments the small diameter sections may be of different length to discharge different amounts of liquid to the respective receptacles. For calibration the effective length of each small diameter section may be changed merely by trimming off the tip.

Preferably each tubing 41 is made of a resilient elastomeric material that is inert chemically and biologically, has good resistance to temperature and wear by flexure, and will not take a set when clamped to flow blocking position. Polyethylene and silicone rubber for example are suitable materials.

Figure 3:
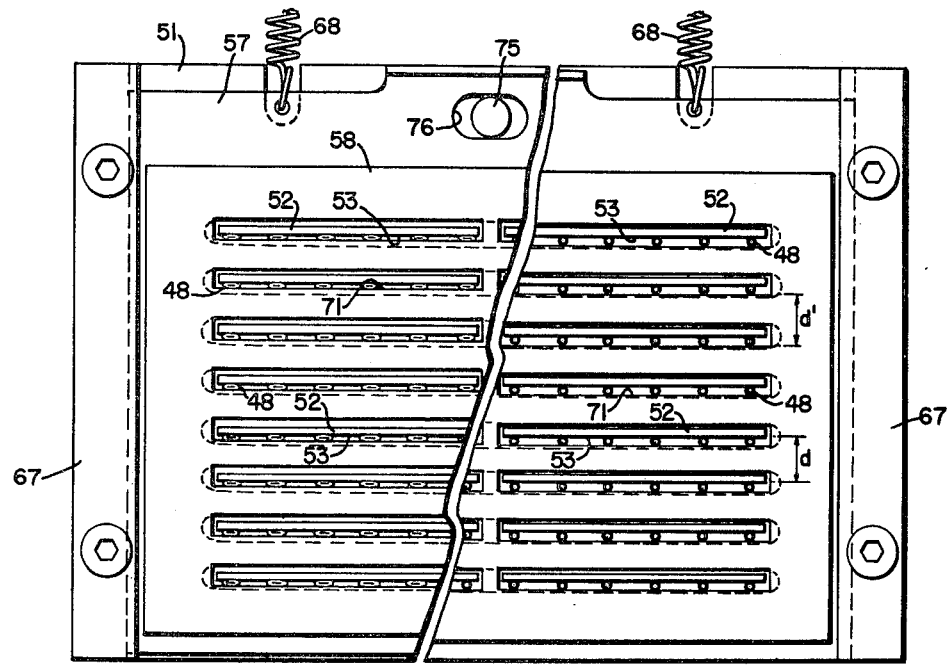
FIG. 3 is a bottom plan view of the pinch valve assembly, broken to show closed and open valve positions.

The discharge ends of the tubing end sections 48 extend snugly through a series of holes 49 in a fixed horizontal valve plate 51 suitably secured on frame 30. As shown more clearly in FIG. 1A, a plurality of identical transverse depending ribs 52 are formed integral with the bottom of plate 51. Since plate 51 has ninety-six circular holes 49 arranged in eight transversely extending rows of twelve rows each, there are eight transverse ribs or fences 52 of the same size (FIG. 3). Ribs 52 accurately formed with flat side faces 53 that are parallel to each other with adjacent faces very accurately equally spaced. Each face 53 lies in a plane substantially tangent to circular holes 49 in its associated row so that, as indicated in FIG. 1A, the terminal 54 or tip of each tubing section 48 lies in a substantial contact on one side with a rib face 53. FIG. 1A illustrates at the right side the valve open condition of each dispensing tubing tip, and at the left side the valve closed condition of each tubing tip.

In practice it has been found important that the spacing between adjacent parallel rib surfaces 53, indicated at d in FIG. 3A, be accurate within ±0.001 inches.

Holes 49, as viewed from above in FIG. 2, are the same in number and arranged in the same relative location as the tips of tubing 48, and their location and spacing is exactly that of the wells in the test tray 50 to which liquid from the containers is to be transferred.

Ribs 52 in effect define a series of transverse parallel recesses 55 on the bottom of the fixed valve plate 51. A reciprocable valve plate unit 56 consisting of an upper rigid plate 57 to the bottom of which is secured as by brazing or welding a relatively thin metal pinch plate 58 is mounted on the bottom of fixed valve plate 51. Plate 57 is formed with transverse apertures 59 that are wide enough to clear ribs 52 in all positions of valve plate 56 so that valve plate 56 may be physically disposed within recesses 55 for operative reciprocation in a plane as close as possible to the tips of tubing 48 and have sufficient clearance with respect to the ribs to enable plate 56 to reciprocate adequately in operation.

Figure 4:
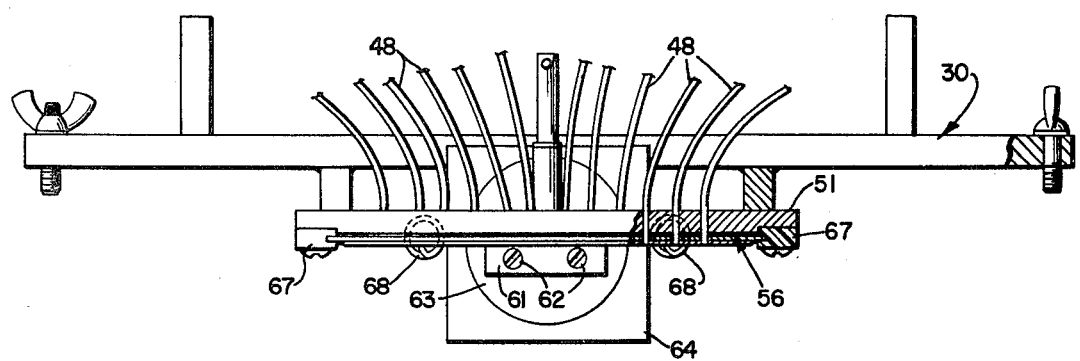
FIG. 4 is an end view partly broken away and sectioned showing some of the pinch valve assembly in further detail.

At one end reciprocable plate 57 is formed with a right angle flange 61 secured as by screws 62 to a piston 63 reciprocable in a cylinder 64 mounted on frame 30. A chamber 65 within cylinder 64 is supplied with fluid under pressure through a pneumatic fitting 66. The side edges of plate 57 are slidably supported in parallel plastic coated smooth guides 67 (FIG. 4) fixed on plate 51.

At its rear end plate 57 is connected by parallel laterally spaced coil tension springs 68 to posts 69 rigid with fixed valve plate 51, so that the valve plate unit 56 is normally spring biased to the right in FIG. 1 to the valve closed position also shown in at the left side of FIG. 1A to pinch the ends of tubing sections 48 flat and tight against rib faces 53.

Referring to FIGS. 1A and 3, it will be noted that the thin plate 58 is formed with apertures 71 that overlap the apertures in plate 57 along one side, so that when fluid pressure is applied to cylinder 64 to displace valve plate unit 56 against the action of springs 68 only a relatively short area of terminal 54 at substantially the tip of each resilient tubing end 48 is clamped flat due to the fact that plate 58 is relatively thin and located on the bottom of plate 57. In practice plate 58 may be only about 0.005 to 0.010 inches in thickness. The tubing contacting edges 72 along apertures 71 are parallel and accurately spaced apart a distance d' with the same tolerances as the spacing of rib faces 53, and it is the foregoing construction of valve plate unit 56 that permits this accuracy. The apertures 71 may be formed in thin plate 58 by a photoetching operation with greater accuracy in tubing contacting edge spacing than they can be formed in a thicker plate by machining. Thus the foregoing structure of the valve plate 56 provides for more accurate valve closing in that it limits the amount of tubing that has to be pinched to obtain valve closure, it reduces the force necessary to close the tubing, and it minimizes the time that the tubing takes to spring open when fluid pressure is applied to the piston and displaces the valve plate.

By making the valve with the high degree of accuracy above detailed it is possible to obtain exactly similar opening and closing conditions in each of the ninety-six tips of tubing 48. Since the resilient tubing 48 is pinched at the discharge terminals the necessity for special nozzles is entirely eliminated. The liquid in each tubing is under pressure from chamber 28 so that the column of liquid therein is free of air bubbles, and by pinching each tubing to closed condition in very narrow regions at the extreme tips the closing action squeezes the liquid in those regions out as droplets from the tubing ends to thereby eliminate the entrance of air bubbles as well as contribute to accuracy of metering. Thus discharge is accurately metered and there is no waste of valuable or expensive liquid.

The degree of valve opening during each dispensing operation may be varied by provision of an adjustably mounted eccentric stop 60 in the path of valve plate 56 shown in fully open position in FIG. 1. By turning stop 60 the stroke of the piston may be selected to permit various partial opening of all of the tubing ends at once. A micrometer adjustment may be provided here suitably calibrated and marked with a scale. In one position this stop may serve as the fully open limit stop. The degree to which the tubing ends are squeezed may be controlled by an adjustable stop 65' limiting movement of the piston to the right of FIG. 1.

The movable valve plate unit 56 may be manually moved to valve open position. This enables the tubing tips to expand to non-pinched condition when the valve is idle or in storage, thereby eliminating possible permanent deformation. A stem 73 is rotatably mounted in a column 74 fixed to plate 51 and carries on its lower end an eccentric button 75 disposed in a noncircular slot 76 in plate 57. When stem 73 is rotated it displaces the unit 56 between the valve closed and valve open positions illustrated at the respective left and right sides in FIG. 3.

The test tray 50 of the movable test tray assembly 22 is immovably mounted on a slidable carrier 77 having a pull handle 78. Advantageously the bottom of the tray 50 and the top surfaces of the carrier are provided with keying formations so that the tray may assume only one position on the carrier and thereby present the wells in exactly the same arrangement as the supply containers.

Carrier 77 is pulled out fully to place the tray 50 thereon and when pushed in fully each well 84 of the test tray is located accurately just below the end of a tubing section 48. In the embodiment being described, the carrier is slidably mounted by means of a ball bearing slide 79 on a fixed support 30' rigid with frame 30. Carrier 77 is formed with an upwardly facing recess 81 connected by a conduit 82 to a liquid collect reservoir 83 for carrying away liquid discharged from the tubing when the tubing is primed with no test tray 50 in place before beginning operation. Suitable stops 80' and 80" respectively on carrier 77 and support 30' engage to limit inward movement of carrier 77.

OPERATION

In the illustrated embodiment the chamber 28 is pressurized thereby forcing liquid from each container through the associated tubing 41 toward the valve 46.

When the valve is idle stem 73 is normally turned so that the tips of tubing 48 are not pinched shut, the parts then being in the condition shown at the right of FIG. 1A. At the beginning of the operation period, stem 73 is turned to release position and the tubing tips are clamped shut as illustrated at the left side of FIG. 1A because under the influence of springs 68 valve plate 56 is displaced to the right in FIG. 1. After the tubing contains liquid, stem 73 may be actuated to momentarily allow the tubing tips to spring open and thereby prime the tubing and then returned to release position.

The tray 50 is placed on carrier 77 which is pushed in to dispose the wells 84 each beneath a tubing end.

Now the valve is opened for a predetermined small period, sufficient to allow each tubing to discharge into its associated well 84, and then closed. This may be done by controlled pressured operation of piston 63 to effect the opening stroke, the springs 68 effecting the valve closing stroke.

FURTHER EMBODIMENT

Figure 5:
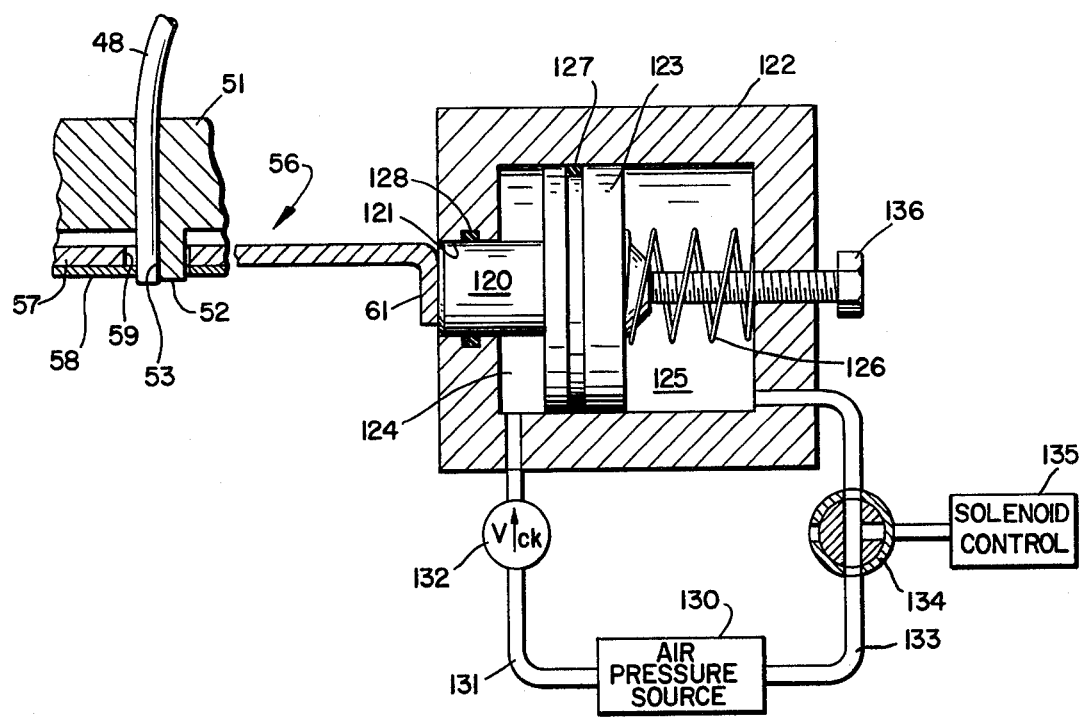
FIG. 5 is a mainly diagrammatic fragmentary view in section showing a fluid pressure responsive actuator for the valve.

FIG. 5 illustrates another and mainly preferred mode for actuating the valve.

The flange 61 at the end of valve plate 56 is fixed to the end of a piston rod 120 slidable in an end bore 121 of a cylinder 122 and fixed to piston 123 reciprocable within the cylinder. Piston 123 separates the cylinder into chambers 124 and 125. A biasing compression spring 126 in chamber 125 urges the piston to the left in FIG. 5. Piston 123 has a sliding peripheral seal at 127 with the cylinder wall, and piston rod 120 has a slidable seal at 128 in bore 121.

A source of compressed air 130 maintained at a constant pressure P is connected to chamber 124 by a conduit 131 containing a check valve 132, whereby chamber 124 may be instantly and always pressurized whenever the apparatus is operated. A conduit 133 containing a solenoid operated valve 134 is connected to chamber 125. Valve 134 is normally disposed to close conduit 133 and to vent chamber 125 to atmosphere. Valve 134 may be actuated as shown in FIG. 5 to periodically close the vent to atmosphere and open conduit 133 to supply air pressure to chamber 125 for a predetermined small period, as by timed pulses from a control diagrammatically shown at 135. The force exerted on the piston by fluid pressure in chamber 124 is greater than the opposite force of spring 126. An adjustable stop 136 controls the displacement of piston 123 to the right in FIG. 5 and thereby determines the degree to which the ends of tubes 48 are compressed.

Normally when the apparatus incorporating the dispensing valve of the invention is not in use, as shown in FIG. 5 the air pressure source 130 is inactive or isolated so that no compressed air is transmitted to either cylinder chamber. The spring 126 at this time biases piston 123 to the left in FIG. 5 thereby automatically displacing valve plate 56 to the illustrated release position where it does not pinch the end of the tubing 48. This valve open condition corresponds to that shown at the right side in FIG. 1A. Obviously spring 126 will overcome the force exerted by springs 68 if the latter are used.

When the operator starts to use the apparatus the compressed air source 130 is activated, thereby immediately establishing a pressure P in chamber 124 and, since valve 134 at this time continues to block conduit 133 and chamber 125 is at atmospheric pressure, the force exerted by the pressure in chamber 124 overcomes the spring force at 126 and piston 123 is automatically displaced to the right to pinch the ends of tubing 48 closed. This movement is aided by springs 68. This corresponds to the valve closed starting condition shown at the left side of FIG. 1A. Spring 126 is compressed and further energized by this movement of the piston.

The valve discharge cycle during operation is controlled by pulses from control 135 which act to periodically move valve 134 to periodically pressurize chamber 125 at pressure P whereby the combined forces of fluid pressure and spring 126 in chamber 125 are effective to displace valve plate 56 for small periods each sufficient to allow all of the tubing ends 48 to spring open and discharge the required small amount of liquid into each of the tray wells simultaneously. Then the valve 134 is returned to starting position whereby chamber 125 is depressurized to atmospheric pressure and the pressure in chamber 124 acts to immediately reclose the tubing ends. When piston 123 is moved to the left, due to the fact that check valve 132 effectively closes conduit 131 against exhaust of chamber 124, the air in chamber 124 is compressed further and in effect constitutes a shock absorber. On the other hand the compressed air body in chamber 124 acts as an air spring that, when chamber 125 is depressurized, instantaneously starts and accelerates movement of the valve plate.

The cycle may be repeated manually or automatically depending upon the apparatus and desired operation.

When the operation is complete and air pressure source 130 is disabled chamber 125 is connected to atmosphere, and valve 132 gradually leaks the pressure from chamber 124 until spring 126 may move the valve plate to the release position shown in FIG. 5. This gradual release is advantageous because it permits time for deenergization of chamber 28 by the time the pinch valve opens.

The foregoing valve structure is highly efficient for the repeated accurate simultaneous dispensing of very small quantities of liquid. Only a low pinch force is required at a very small region at the tip of each tubing 48 when the valve is being closed, and the tubing springs open by its own elasticity and without any mechanical aid. The valve parts including the piston are of low mass, whereby there is provided a low inertia system capable of direct fast response and high acceleration for reduced response time.

The dispensing region is remote from the valve actuator which prevents undesirable exposure of the liquid being handled to heating from the actuator. While a pressure responsive actuator is preferred, in some apparatus solenoid or other motor operation may be adequate.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Apparatus for the rapid accurately metered dispensing of separate small amounts of liquid comprising a pinch valve having two relatively movable members, a plurality of individual liquid conducting conduits having resilient discharge terminals extending in closely spaced relation between said members, and actuating means for relatively moving said members between a valve closed position wherein all of said terminals are pinched shut between said members and a separated valve open position wherein said terminals are all free to spring to open condition, one of said pinch valve members being a reciprocable member and said actuating means comprising a piston connected to said reciprocable member and slidable in a cylinder, the interior of the cylinder being separated by said piston into two chambers, resilient means in one of said chambers biasing said piston in the direction to displace said reciprocable member to said valve open position, means for introducing air under pressure into the other chamber through a check valve, said air pressure exerting a force on said piston greater than said resilient means whereby said piston may be moved in the direction to displace said reciprocable member to pinch said terminals shut, and means for periodically introducing fluid pressure into said one chamber whereby the combined forces of fluid pressure and resilient means in said one chamber may periodically move said piston to displace said reciprocable member sufficiently to release all of said terminals for discharge of liquid during each period.

2. The apparatus defined in claim 1, wherein adjustable stop means is provided in the path of said piston when it is moved in the direction to pinch said terminals shut whereby to control the degree of compression of said terminals.

3. Valve means for simultaneously dispensing a multiplicity of charges of liquid comprising a relatively fixed member having a plurality of spaced apertures arranged in a plurality of linear rows, means on one surface of said member providing fixed depending ribs each extending along a side of a row of said apertures, a corresponding multiplicity of resilient liquid conducting tubing end sections extending downwardly through said apertures so that the terminal of each tubing end section lies adjacent a rib with one side adapted to engage the rib, a valve member having apertures located correspondingly to the apertures in said fixed member mounted below said fixed member to reciprocate in a plane transversely of said fixed member, said valve member having surfaces at its apertures disposed to engage said tubing terminals at the sides opposite the ribs, means for holding said valve member in the position where it tightly presses the tubing terminals against the ribs to effect valve closing, and means for periodically reciprocating said valve member to release and open said tubing to discharge liquid from each tubing at the same time.

4. The valve means defined in claim 3, wherein said valve member comprises a rigid support plate formed with a series of linear apertures and said surfaces are on the side edges of substantially linear apertures formed in a relatively thin plate fixed upon the lower face of said support plate, said thin plate being so disposed upon the rigid support plate that the apertures overlap with said surfaces lying within the downwardly projecting areas of said support plate apertures, whereby the effective tubing gripping area is minimized and located as near as possible to the tubing ends.

5. In the valve means defined in claim 3, said ribs having parallel smooth tubing engaging surfaces that are perpendicular to the direction of reciprocation of the valve member with adjacent surfaces spaced accurately the same distance apart.

6. In the valve means defined in claim 3, said means for periodically reciprocating said valve member comprising a fluid pressure responsive element connected to said valve member spring biased in the direction to open said tubing ends and in combination with means whereby selectively applied fluid pressure initially displaces said valve member to close said tubing ends and time controlled means is connected for periodically applying fluid pressure to said element to displace said valve member to tubing open position for a limited liquid discharge period.

7. Valve means for simultaneously dispensing a multiplicity of charges of liquid comprising a relatively fixed member having a plurality of apertures arranged in a plurality of linear rows, means on said member providing fixed parallel tube pinching surfaces each extending along a side of a row of said apertures, a corresponding multiplicity of resilient liquid conducting tubing end sections extending downwardly through said apertures so that the one side of the terminal of each tubing end section lies closely adjacent a pinching surface, a valve member having linear apertures located correspondingly to the apertures in said fixed member mounted below said fixed member to reciprocate in a plane transversely of said pinching surfaces, said valve member having parallel tube pinching surfaces along its apertures disposed to engage the opposite sides of said tubing terminals, means for holding said valve member in the position where it tightly clamps the tubing terminals to effect valve closing, and means for periodically reciprocating said valve member to release and open said tubing to discharge liquid from each tubing for a predetermined period at the same time.

8. In the valve means defined in claim 7, said means for periodically reciprocating said valve member comprising a fluid pressure responsive element connected to said valve member spring biased in the direction to open said tubing ends and in combination with means whereby selectively applied fluid pressure initially displaces said valve member to close said tubing ends and time controlled means is connected for periodically applying fluid pressure to said element to displace said valve member to tubing open position for a limited liquid discharge period.

* * * * *